United States Patent
Robichaud et al.

(10) Patent No.: US 6,316,434 B1
(45) Date of Patent: Nov. 13, 2001

(54) ASSAY FOR EMETIC ACTIVITY

(75) Inventors: Annette Robichaud, Montreal; Chantal Savoie, St. Lazare; Chi Chung Chang, Kirkland, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/512,513

(22) Filed: Feb. 24, 2000

Related U.S. Application Data

(60) Provisional application No. 60/122,708, filed on Mar. 3, 1999, now abandoned.

(51) Int. Cl.$^7$ .......................... A01N 43/00; A01N 43/40; A01N 61/00; C12Q 1/68; G01N 3/543
(52) U.S. Cl. .................. 514/183; 514/1; 514/44; 514/77; 514/277; 435/6; 435/7.1; 435/7.2; 436/518; 436/528; 422/55; 422/67; 422/82.05; 422/82.09
(58) Field of Search .................... 514/1, 44, 77, 514/183, 277; 435/6, 7.1, 7.2; 436/518, 528; 422/55, 67, 82.05, 82.09

(56) References Cited

U.S. PATENT DOCUMENTS

| | | | |
|---|---|---|---|
| 5,608,070 | 3/1997 | Alexander et al. | 546/270 |
| 5,632,977 | 5/1997 | Chandran et al. | 424/70.17 |
| 5,710,160 | 1/1998 | Guay et al. | 514/277 |
| 5,710,170 | 1/1998 | Guay et al. | 514/332 |
| 6,034,089 | 3/2000 | Han et al. | 514/269 |

OTHER PUBLICATIONS

A.J. Duplantier et al., J. Med. Chem., 39:120–125 (1996).
L. Sekut et al., Lab. Animal Sci.,45:647–651 (1995).
R.J. Heaslip et al., Eur. J. Pharmacology, 286:281–290(1995).
P.L.R. Andrews and C.J. Davis, "The physiology of emesis induced by anti–cancer therapy," *Serotonin and the Scientific Basis of Anti–emetic Therapy* (D.J.M. Reynolds et al., Eds.) pp. 25–49, Oxford Clinical Communications, (Oxford, 1995).
E. Zaller et al., Pharmacopyschiat., 17:188–190 (1984).
C. Correa–Sales et al., J. Pharmacology and Exp. Therapeutics, 263:1046–1049 (1992).
C.D. Nicholson et al., Pulmonary Pharmacology, 7:1–17(1994).
B.V. Clineschmidt et al., J. Pharmacology and Exp. Therapeutics, 245:32–40(1988).
Y. Hikasa et al., Am. J. Vet. Res., 50:1348–1351 (1989).
M. Humpel et al., Arch. Toxicol., 59,Suppl.9:251(1986).
P.L. Harbinson et al., Eur. Respir. J., 10:1008–1014(1997).
T.J. Sylvina et al., Lab. Animal Sci.,40:178–182(1990).
J. Silvestre et al., Drugs of the Future, 23:607–615(1998).
C. Saoie et al., Can. J. Physiol, Pharmacol., 78:708–71(2000).
D.J. Pettibone et al., Arch. Pharmacol., 336:169–175(1987).

(List continued on next page.)

*Primary Examiner*—Jezia Riley
(74) *Attorney, Agent, or Firm*—Shu M. Lee; David L. Rose

(57) ABSTRACT

An assay for emetic activity among inhibitors of type 4 phosphodiesterase (PDE 4) is disclosed. The assay comprises:

(A) administering to a test mammal an anesthetic compound in an amount sufficient to cause an anesthetic effect;

(B) administering to the test mammal a test compound that has PDE 4 inhibitory activity;

(C) observing the test mammal for changes in the anesthetic effect, and (D) correlating any change in the anesthetic effect observed in the anesthetized test mammal to a standard.

12 Claims, 2 Drawing Sheets

OTHER PUBLICATIONS

R.B. Nieman et al., Am. J. Respir. Crit. Care. Med., 157:A413(1998).
R.D. Murdoch et al., Am. J. Respir. Crit. Care Med., 157:A409(1998).
S.Z. Langer, Pharmacol. Rev., 32:337–362(1981).
Y. Hikasa et al., J. Pharmacology and Exp. Therapeutics, 261:746–754(1992).
S. K. Khandker et al., Pharmacol. Res.,29:383–387(1994).
J-A Karlsson et al., Exp. Opin. Ther. Patents, 7:989–1003(1997).
N. Japundzic–Zigon et al., Pharmacol.Res., 35:287–297(1997).
R. Horowski et al., Curr. Therapeutic Res.,38:23–29(1985).
Y. Hikasa et al., Eur. J. Pharmacology,229:241–251(1992).
R.E. Fish, "Pharmacology of Injectable Anesthetics," *Anesthesia and Analgesia in Laboratory Animals* (D.F. Kohn et al., Eds.) pp. 1–8, Academic Press (New York, 1997).

ASSAY FOR EMETIC ACTIVITY

This application claims the benefit of U.S patent application No. 60/122,708, filed Mar. 3, 1999, now abandonded.

BACKGROUND OF THE INVENTION

The present invention relates to an assay for detecting emetic activity in test compounds that are useful as type 4 phospodiesterase (PDE 4) inhibitors. Such compounds have important biological activity and can be used in treating or preventing asthma and other inflammatory diseases and conditions. (Harbinson et al., 1997; Karlsson & Aldous, 1997; Silvestre et al., 1998; Nieman et al., 1998; Nicholson & Shadid, 1994). However, these agents are known to cause emesis in man and in various animal species (Silvestre et al., 1998; Murdoch et al., 1998; Robichaud et al., 1998; Heaslip & Evans, 1995; Humpel et al., 1986; Horowski & Sastrey-Hernandez, 1985). This debilitating side effect is a great impairment to the therapeutic potential of this new class of drugs.

Consequently, one object of the present invention was to elucidate the mechanism by which PDE 4 inhibitors trigger emesis.

Another object was to provide an assay for emesis that is reliable.

More particularly, an object of the present invention was to investigate the involvement of the noradrenergic nervous system in PDE 4 inhibitor-induced emesis and to provide an assay for emetic activity in these compounds.

Further, this assay is particularly useful for the identification of the locus of action of test compounds.

According to an aspect of the invention, the present assay is useful in identifying a test compound having activity in a cerebral and/or a peripheral locus of action. Therefore it is a useful application to select a test compound that is capable of crossing the blood-brain barrier.

These and other objects will become apparent to those of ordinary skill from the teachings provided herein.

SUMMARY OF THE INVENTION

The present invention encompasses an assay for emetic activity of a PDE 4 inhibiting compound, comprising:

(A) administering to a test mammal an anesthetic compound in an amount sufficient to cause an anesthetic effect;

(B) administering to the test mammal a test compound that has PDE 4 inhibitory activity;

(C) observing the test mammal for changes in the anesthetic effect, and (D) correlating any change in the anesthetic effect observed in the anesthetized test mammal to a standard.

BRIEF DESCRIPTION OF THE DRAWINGS

The invention is illustrated in connection with the drawings in which.

DETAILED DESCRIPTION

Figure 1:
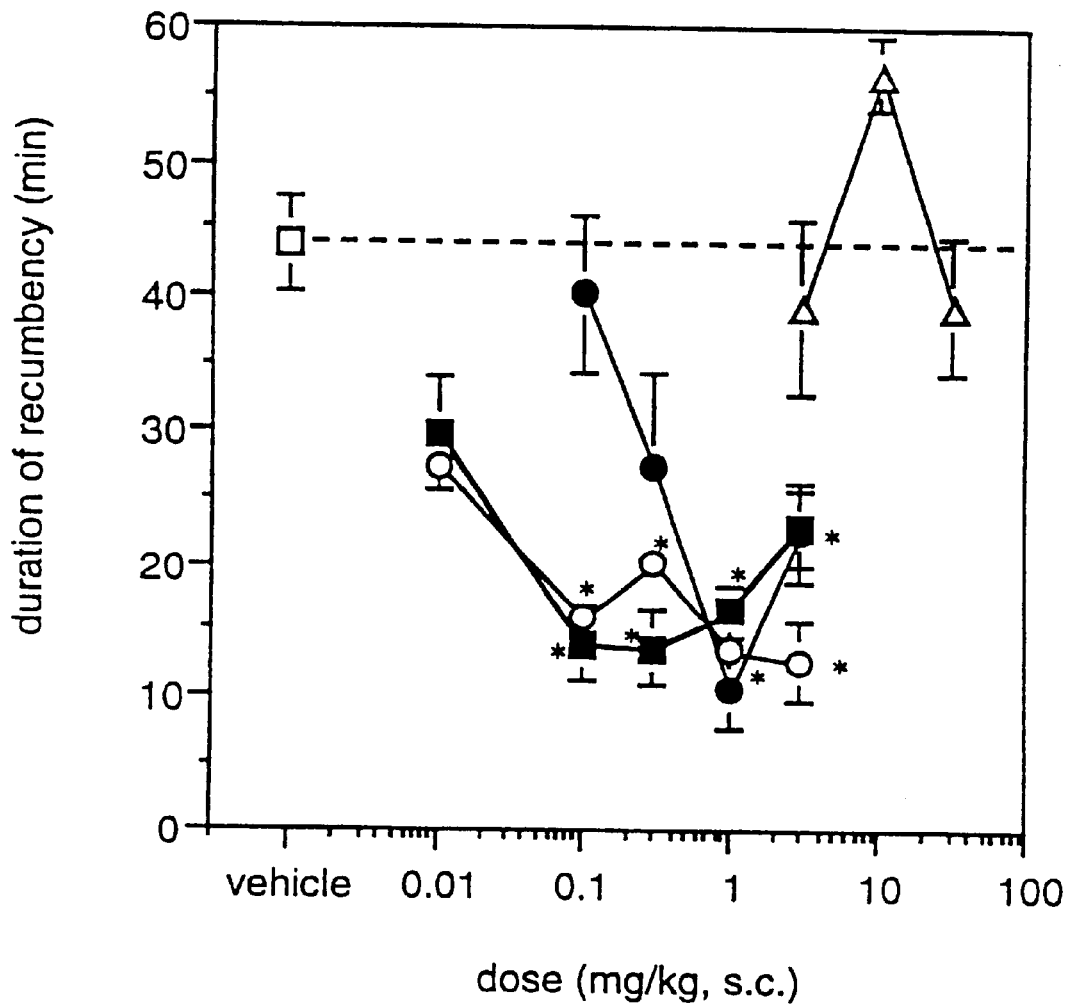
FIG. 1 is a graph of the effect of PDE 4 inhibitors on the duration of xylazine (10 mg/kg)/ketamine (10 mg/kg) anesthesia in rats. Fifteen minutes following the induction of anesthesia, rats were injected with: ▫ vehicle (60% PEG-200, n=14); ■ RS-14203; ○ R-rolipram; ● S-rolipram; or Δ CT-2450. The duration of anesthesia was assessed by the return of the righting reflex. Data is expressed as mean±SEM, with 4–9 animals/dose tested. *Statistical difference from vehicle group at p<0.05 (ANOVA) and FIG. 2 and FIG, 3 are graphs of the effect of alpha-2 adrenoceptor antagonists, MK-912 and MK-467 respectively, on the duration of xylazine (10 mg/kg)/ketamine (10 mg/kg) anesthesia in rats. Fifteen minutes following the induction of anesthesia, rats were injected with: A. MK-912, B. MK-467. The duration of anesthesia was assessed by the return of the righting reflex. The vehicle used for MK-912 and MK-467 was 60% PEG-200. The results show that animals treated with MK-912 have a short duration of recumbency at low dosing. Treating the animals with MK-467 does not affect the recumbency period when compared to vehicle- treated animals even at high dosing. Data is expressed as mean±SEM. * Statistical difference from vehicle group at p<0.05 (ANOVA).
Figure 3:
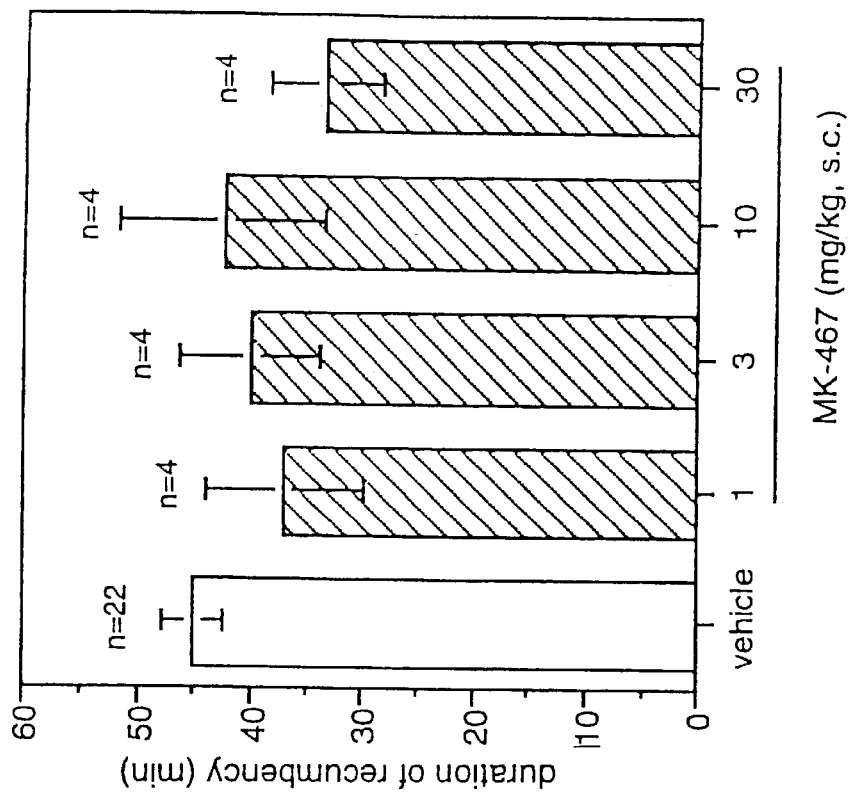

It is recognized that among compounds known as PDE 4 inhibitors, the most common side effect is emesis. The present invention provides an assay that correlates well to emetic effects in this particular drug class.

In one aspect of the invention, an assay for emetic activity of a PDE 4 inhibiting compound is disclosed which comprises:

(A) administering to a test mammal an anesthetic compound in an amount sufficient to cause an anesthetic effect;

(B) administering to the test mammal a test compound that has PDE 4 inhibitory activity;

(C) observing the test mammal for changes in the anesthetic effect, and (D) correlating any change in the anesthetic effect observed in the anesthetized test mammal to a standard.

In another aspect of the invention, an assay is disclosed wherein the anesthetic compound administered to the test mammal in an amount sufficient to cause an anesthetic effect is an alpha-2 adrenoceptor agonist compound selected from the group consisting of xylazine, medetomidine, dexmedetomidine, detomidine and clonidine.

In another aspect of the invention, an assay is disclosed wherein the anesthetic alpha-2 agonist compound is administered with an anesthetic selected from the group consisting of: ketamine, phencyclidine and tiletamine.

In another aspect of the invention, an assay is disclosed wherein the step of observing the test mammal for changes in the anesthetic effect is comprised of placing the test mammal in dorsal recumbency and observing for restoration of the righting reflex. As used herein, the duration of dorsal recumbency is equivalent to the time for restoration of righting reflex.

In another aspect of the invention, an assay is disclosed wherein the restoration of the righting reflex is correlated with the propensity of the test PDE 4 inhibiting compound to cause emesis.

In another aspect of the invention, an assay is disclosed wherein the test mammal is selected from the group consisting of; rats, mice and ferrets.

As described herein, there is a good correlation between a modulation of the anesthetic effect of alpha 2 adrenoceptorr agonist anesthetics and the emetic effect of PDE 4 inhibitors.

Examples of compounds having PDE 4 inhibitory activity can be found in U.S. Pat. Nos. 5,710,160 and 5,710,170, granted on Jan. 20, 1998, U.S. Pat. Nos. 5,608,070, 5,632, 977 granted on Apr. 22, 1997, and in U.S. application Ser. No. 09/163,033, filed on Sep. 28, 1998, all of which are incorporated herein by reference their entirety.

Rolipram, RS14203, and CT-2450 are known PDE 4 inhibiting compounds. The structures are shown below.

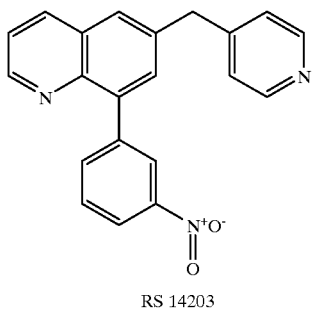

RS 14203

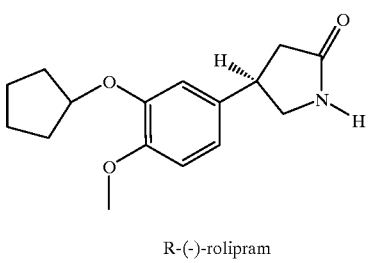

R-(-)-rolipram

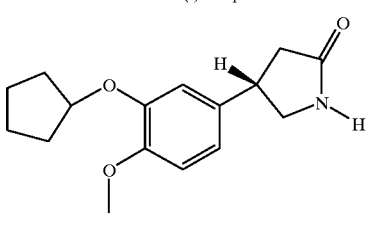

S-(+)-rolipram

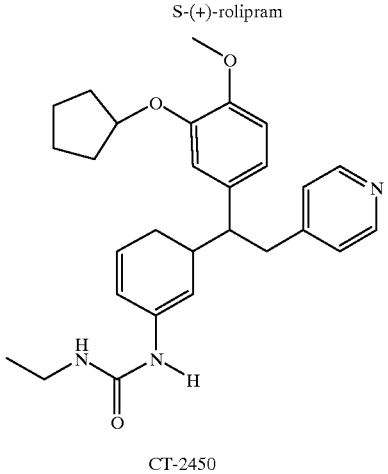

CT-2450

MK-912 and MK-467 have the following structures:

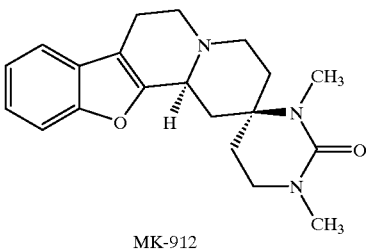

MK-912

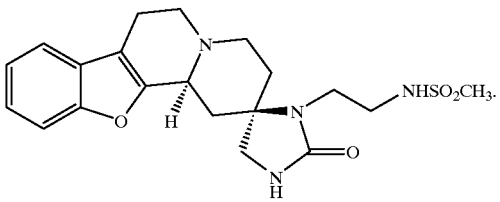

MK-912

As used herein, "emetic activity" in non-human mammals refers to retching, vomiting, excessive salivation, hyperventilation, gagging and clawing at the mouth. In humans this refers to retching, vomiting, nausea and the like.

Clonidine is a known alpha 2 adrenoceptor agonist that does not serve generally as an anesthetic. Rather, it acts as an antihypertensive. Xylazine is another known alpha 2 adrenoceptor agonist, that is useful in veterinary medicine as an anesthetic.

It has been observed that PDE 4 inhibitors that have less emetic activity do not reduce the anesthetic effect that is observed with Xylazine/ketamine in test mammals as much as PDE 4 inhibitors that have a greater propensity to cause emesis. PDE 4 inhibitors that have a greater emetic effect cause the test mammals to regain the righting reflex more quickly. Thus, there is a correlation between the potential to cause emesis and the shortening of the anesthetic effect. Without being limited to a particular mechanism of action, one explanation for the correlation between changes in the anesthetic effect of alpha 2-adrenoceptor antagonist anesthetics and emesis observed with PDE 4 inhibitors is that the PDE 4 inhibitors trigger emesis by mimicking the biological actions of alpha 2-adrenoceptor antagonists. This has been demonstrated in rats and ferrets. Struturally different PDE 4 inhibitors effect on xylazine/ketamine anesthesia in rats and ferrets were used. RS14203, R-rolipram and S-rolipram dose-dependently decreased the duration of recumbency of rats anaesthetized with the combination xylazine/ketamine. CT-2450, the PDE 4 inhibiting compound described herein that has the lowest propensity to cause emesis, was without effect on the restoration of the righting reflex at the doses tested (3–30 mg/kg).

Test compounds can be effective at a peripheral and/or a cerebral locus of action. In an application of this assay, the locus of action of the test compound can be characterized. In a further aspect of this application, it has been observed that test compounds capable of affecting the cerebral locus of action, and therefore demonstrating an ability to cross the blood-brain barrier, reduce the anesthetic effect that is observed with xylazine/ketamine in test mammals. Test compounds affecting only a peripheral locus of action have no effect on the duration of xylazine/ketamine induced anesthesia in test mammals.

Compounds having PDE 4 inhibitory activity can be characterized using the following assay protocols.

Assays for Determining PDE 4 Inhibitory Activity

Establishment of CHO-K1 cell lines stably expressing PDE4a Enzyme

CHO-K1 cells stably expressing the prostacyclin receptor and grown under G418 selection as described previously (Y. Boie, et al, J. Biol. Chem.: 269, 12173–12178, 1994) were plated at a density of $1.75 \times 10^6$ cells/175 $cm^2$ in a T-175 flask (Gibco, Burlington, Vt.) containing alpha MEM media; 10% heat inactivated fetal bovine serum (FBS); 1% (v/v)

penicillin/streptomycin; 25 mM Hepes, pH 7.4; and 500 mg/ml G418 (complete media). The cells were placed in an incubator for 24 hr at 37° C. and 5% $CO_2$. The cells were then washed with warmed sterile phosphate buffered saline (PBS) and incubated with 2 mg/ml DNA, and 9 mg/ml lipofectamne reagent in Opti-MEM for 7 hr. At 37° C. and 5% $CO_2$. The incubation solution was diluted 1:2 with Opti-MEM containing, 20% FBS and incubated overnight. Following the overnight incubation, the media was replaced by complete media containing 500 mg/ml hygromycin B. Colonies were identified and grown in T-175 flasks for further characterization.

Measurement of Whole-cell cAMP Content

CHO-K1 cells were plated at a density of $10^6$ cells/175 $cm^2$ containing complete media with 500 mg/ml hygromycin. The flasks were maintained in an incubator at 37° C. with 5.0% $CO_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of $0.2 \times 10^6$ cells/ml. The cells were preincubated at room temperature for 15 min. and then incubated with 10 mM prostaglandin $I_2$ ($PGI_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 ml reconstituted rabbit anti-succinyl cAMP serum with 100 ml of the whole-cell reaction or known cAMP standard and 30 pmol of $^{125}$-IcAMP TME in a ScintiStrip™ well (300 ml final volume) at room temperature for 18 h. Total cpm ($B_o$) was determined in the absence of sample of cAMP standard. The reaction mixture was then aspirated out of the well, and the individual wells were counted in a Beckman LS 6000SC with the window open from 10–999 for 1 min. The data were expressed as % $B/B_o$=[(standard or sample cpm-non-specific cpm)/($B_O$ cpm-non-specific cpm)]×100. Non-specific cpm were determined by incubating only the $^{125}$I-cAMP TME with assay buffer (50 nM acetate; pH 5.8) in the ScintiStrip™ well. All determinations were performed in triplicate.

Phosphodiesterase Scintillation Proximity Assay

CHO-K1 cells were lysed by sonication for 10 secs at a power setting of 50% (Braunsonic Model 2000) in an ice cold Solution containing 50 mM Tris, pH 7.5; 1 mM EDTA; and 200 mM b-mercaptoethanol. The soluble and particulate fractions of the cell were obtained by centrifuging the sonicate for 90 min. at 100,000×g at 4° C. PDE activity was measured in a solution containing 50 mM Tris, pH 7.5; 10 mM $MgCl_2$; 1 mM EDTA; and 100 nM (or indicated) $^3$H-cAMP (100 ml final volume) in the presence of varying concentrations of inhibitor. The reaction mixture containing enzyme was incubated for 10 min. at 30° C. in 96-well View Plates (Packard), and terminated by the addition of 50 ml Phosphodiesterase Scintillation Proximity Assay (SPA) Beads (Amersham) containing 18 mM $ZnSO_4$. The amount of $^3$H-cAMP hydrolysis was determined by counting the plates in a Wallac 1450 mBeta LSC counter.

The Elevation of cAMP in Leukocytes

The effect of PDE 4 inhibitory compounds on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

Suppression of Leukocyte Function

PDE 4 inhibitory compounds were investigated for their effects on superoxide generation, chemotaxis and adhesion of neutrophils and eosinophils. Isolated leukocytes were incubated with dihydrocyto-chalasin B for superoxide generation only and test compound prior to stimulation with FMLP.

Lipopolysaccharide (LPS)-induced synthesis of tumor necrosis factor (TNF) by human peripheral blood monocytes (PBM) is inhibited by PDE 4 inhibitory compounds.

Relaxation of Constricted Airway Smooth Muscle in vitro

The effects of PDE 4 inhibitory compounds on guinea-pig isolated tracheal smooth muscle were investigated. Isolated tracheal rings were suspended in organ baths and immersed in oxygenated Krebs' solution. The smooth muscle was contracted with sub-maximal concentrations of histamine or carbachol prior to the addition of increasing concentrations of test compound to the organ baths. The compounds caused a concentration-dependent reversal of both histamine and carbachol-induced contractions.

Effects on Cardiac Muscle in vitro

PDE 4 inhibitory compounds have also been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE 4 inhibitors such as rolipram do not have any direct effects whereas selective PDE III inhibitors such as milrinone have positive chronotropic and inotropic effects. The non-specific PDE inhibitor theophylline, which is used in asthma as a bronchodilator, also causes significant cardiovascular changes such as tachycardia. Selective PDE 4 inhibitors have an advantage over theophylline, therefore, through reduced cardiovascular side effects.

Anti-inflammatory Activity in vivo

Interleukin-5 (IL-5)-induced pleural eosinophilia in the rat (Lisle, et al., 1993, *Br. J. Pharmacol.* 108, 230p) is inhibited by compounds having PDE 4 inhibitory activity.

PDE 4 inhibitory compounds can also be shown to reduce the inflammatory responses induced in rats by platelet activating factor (PAF).

Anti-allergic Activity in vivo

PDE 4 inhibitory compounds have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolized ovalbumin whilst under cover of an intrapeitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

Effects on Pulmonary Dynamics

PDE 4 inhibitory compounds (0.001–10 mg/kg by oral or other route of administration) reduce the allergic bronchoconstrictior caused by antigen in sensitized guinea pigs.

PDE 4 inhibitory compounds have been tested for their effects on ozone-induced hyperreactivity of the airways of guinea pigs. Following the inhalation of ozone, guinea pigs become very much more sensitive to the bronchoconstrictor effects of inhaled histamine than naive animals (Yedinea et al., 1992, *Pulmonary Pharm.*, 5, 39). There is a pronounced shift to the left (10–30 fold) of the dose response curve to histamine and a highly significant increase in the maximum increase in pulmonary resistance. Compounds administered 1 h prior to ozone by the intraperitoneal or oral (0.001–10 mg/kg) route cause a dose-dependent inhibition of ozone-induced hyperreactivity.

SPA Based PDE Activity Assay Protocol

Compounds which inhibit the hydrolysis of cAMP to AMP by the type-IV cAMP-specific phosphodiesterases were screened in 96-well plate format as follows:

In a 96 well-plate at 30° C. was added the test PDE 4 inhibitory compound (dissolved in 2 ul DMSO) 188 ml of substrate buffer containing [2,8-$^3$H] adenosine 3',5'-cyclic phosphate (cAMP, 100 nM to 50 $\mu$M), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min. at 30° C.). The reaction was stopped after 10 min. by the addition of 1 mg PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the backdground subtracted. Percentage inhibition was calculated accordingly. $IC_{50}$ value was approximated with a non-linear regression fit of the standard 4-parameter/multiple binding sites equation from a ten point titration.

Emesis and Anesthesia Assay Protocols

The emetogenic potential of the PDE 4 inhibitors is correlated to the level of interference that the PDE 4 inhibiting compound demonstrates with the anesthesia achieved with an alpha 2-adrenoceptor agonist anesthetic, such as Xylazine. This is demonstrated using, the following assay protocols.

Emetic Response:

All experimental protocols were approved by the Animal Care Committee at Merck Frosst Centre for Therapeutic Research. Male adult ferrets (*Mustela putorius furo;* 1–2 kg, Marshall Fadinerns, North Rose, N.Y., U.S.A.) were used and experiments were conducted according to procedures previously described (Robichaud et al., 1998). The ferrets were housed in a humidity and temperature controlled environment with food (Marshall Premium ferret diet; Marshall Farms, North Rose, N.Y., U.S.A.) and water provided ad libithum.

Briefly, on the day of the experiment, ferrets were put into individual cages and left to habituate for at least 30 minutes. Fasting was not a pre-requisite of these experiments. Pretreatment with agents of interest or vehicle was performed through a subcutaneous, an intraperitoneal or an oral administration, 60 minutes prior to the emetic challenge. The PDE 4 inhibitors were dissolved immediately before use in 100% PEG-200 and dosed orally at a volume of 1 ml/kg, uSidineng a 40 cm feeding tube (Monoject, St Louis, Mo., USA).

Following the administration of the drugs, the animals were observed continuously up to 120 minutes post-PDE 4 inhibitor dosing. During that time, behavioral changes were recorded, namely the number of retches (i.e. rhythmic contraction of the abdomen) and vomiting movements (i.e. expulsion or attempt to expel solid/liquid matter from the gastrointestinal tract).

Duration of anesthesia

Male Sprague-Dawley rats (338±5 g; Charles River, St-Constant, Qc, Canada) were anaesthetized with a combination of xylazine (10 mg/kg) and ketamine (10 mg/kg) administered in a single intramuscular injection in the back hindlimb. Fifteen minutes later, the drug to be tested or its vehicle was injected subcutaneously (dosing volume=1 ml/kg) and the animals were placed in dorsal recumbency. The duration of anesthesia was measured by the return of the righting reflex i.e. when the animal no longer remained on its back and turned itself completely to the prone position.

The effect of PDE 4 inhibitors on the duration of anesthesia was evaluated in a similar manner in ferrets. Briefly, ferrets were fasted with water ad libitum for at least 8 hours prior to the induction of anesthesia. The animals were anaesthetized with a single intramuscular injection of a combination of xylazine (2 mg/kg) and ketamine (25 mg/kg) in the back hindlimb (Sylvina et al., 1990). Fifteen minutes later, the drug to be tested or its vehicle was administered subcutaneously at the base of the neck, in a dosing volume of 0,25 mil/kg. The ferrets were placed in dorsal recumbency and the duration of anesthesia was assessed by the return of the righting reflex. Each ferret served as its own control and received at random both treatments with a 2 week wash-out period in between treatments. Yohimbine 0.5 mg/kg was used as a positive control.

Drugs

The PDE 4 inhibitors, RS14203, R- and S-rolipram and CT-2450 were supplied by Merck Research Laboratory (Montreal, Qc, Canada). CT-2450 was originally synthesized by Celltech Therapeutics Ltd (Slough, U.K.). MK-912 and MK-467 were obtained from Merck Research Laboratories (Rahway, N.J., U.S.A.). Clonidine was purchased from Sigma (St Louis, Mo., USA), xylazine (Rompun) from Bayer (Etobicoke, Ont., Canada) and ketamine (Ketaset) from Ayerst (Montreal, Qc, Canada).

Data

The incidence (number of responders/number of animals tested) and the latency (time from administration to the first retching or vomiting episode) were calculated. All non-responding animals were given a latency corresponding to the length of the observation period. Values are expressed as means±SEM and were analyzed for significant differences using t-test analysis (paired and unpaired) or analysis of variance (ANOVA) with multiples comparisons (Bonferroni). $P<0.05$ was regarded as being significantly different.

Results

Alpha$_2$- adrenoceptors

Ferrets were pretreated with the alpha 2-adrenoceptor antagonist, yohimbine. Following an intraperitoneal injection, yohimbine unexpectedly induced retching and vomiting in all ferrets treated rapidly after dosing (mean latency=7±1 min). A similar effect was observed whether the drug was administered orally or subcutaneously. Emesis was also recorded following the administration of two other selective alpha-2 adrenoceptor antagonists: MK-912 and MK-467 (Pettibone, et al., 1987; Clineschmidt, et al., 1988).

The alpha2-adrenoceptor agonist, clonidine, was administered to ferrets at doses ranging from 62.5–250 μg/kg. By itself, it did not trigger emesis. However, a light sedation that seemed to be dose-related was rapidly seen Following the administration. Upon challenge with an emetic dose of RS14203 (1 mg/kg p.o.), clonidine caused a dose-dependent decrease in the number of retches (p=0.0009) and vomits (p=0.002) induced by RS14203 and increased the latency of onset (p=0.0001) (Table 1).

Effect of MK-912 and MK-467 on duration of anesthesia

Figure 2:
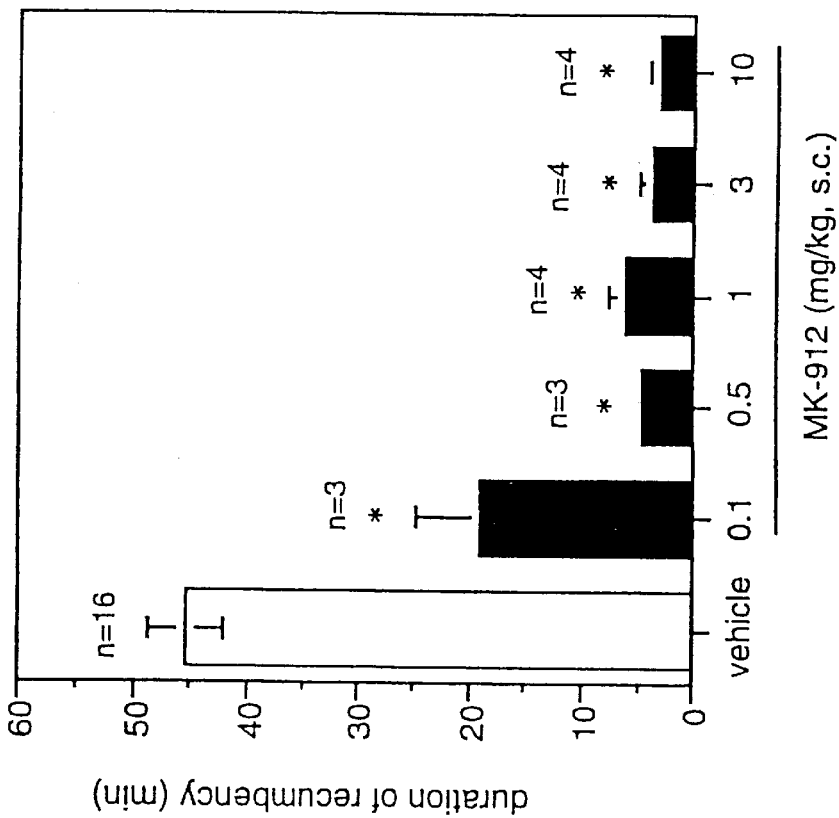

In rats, anesthesia induced by the combination of xylazine and ketamine can be significantly and dose-dependently reversed by the administration of MK-912 but not by MK-467 (FIG. 2). MK-912 has been characterized as a brain penetrant alpha-2 adrenoceptor antagonist (Pettibone et al., 1987), whereas MK-467 is a peripherally active alpha-2 adrenoceptor antagonist (Clineschmidt et al., 1988). The fact that restoration of righting reflex was seen with MK-912, and not with MK-467, suggest that compounds capable of reducing the anesthetic effect of xylazine/ketamine in test mammals are also able to cross the blood-brain barrier.

TABLE 1

Effect of the alpha$_2$ adrenoceptor agonist, clonidine, on emesis induced by PDE 4 inhibitors in ferrets

| Pre-treatment | Dose μg/kg | Emetic agent | Retches no. episodes | Vomits no. episodes | Latency (min) | Incidence[a] |
|---|---|---|---|---|---|---|
| vehicle | — | RS14203 | 29.8 ± 5.9 | 4.8 ± 0.9 | 10.5 ± 5.3 | 6/6 |
| clonidine | 62.5 | RS14203 | 9.3 ± 7.9 | 1.7 ± 1.2 | 77.7 ± 35.6* | 2/3 |
|  | 125 | RS14203 | 2 ± 2* | 1 ± 1* | 104 ± 16* | 1/3 |
|  | 250 | RS14203 | 0.2 ± 0.2* | 0.2 ± 0.2* | 118.5 ± 1.5* | 1/6 |
| vehicle | — | CT-2450 | 24.4 ± 8.6 | 4.0 ± 1.4 | 41.0 ± 20.1 | 4/5 |
| clonidine | 250 | CT-2450 | 0* | 0* | 120* | 0/5 |
| vehicle | — | R-rolipram | 18.3 ± 3.0 | 2.7 ± 0.3 | 25.7 ± 19.8 | 3/3 |
| clonidine | 250 | R-rolipram | 54.3 ± 54.3 | 5.7 ± 5.7 | 81.7 ± 38.3 | 1/3 |

*Statistical difference from vehicle group at $p < 0.05$ (ANOVA or unpaired t-test).
[a]no. responders/no. tested The animals were pretreated 60 min. prior to an emetic provocation with PDE 4 inhibitors (RS14203 1 mg/kg; CT-2450 30 mg/kg; R-rolipram 3 mg/kg). Emesis was monitored for 2 h and all non-responders were attributed a latency of 120 min. Saline was the vehicle used for clonidine and 100% PEG-200 was used for PDE 4 inhibitors. Data is expressed as mean±SEM.

At the highest dose tested (250 μg/kg), five out of six animals pretreated with clonidine showed complete protection against RS14203-induced emesis. The animal that did express an emetic response in that particular group experienced one retching and one vomiting episode. Similarly, clonidine (250 μg/kg) also abolished emesis induced by CT-2450 in all animals treated and provided complete protection in two out of three animals challenged with an emetic dose of R-rolipram.

The administration of RS 14203 to ferrets produced in addition to emesis some other behavioral effects Such as salivation, hyperventilation, gags and clawing at the mouth. These effects were observed in all vehicle- pretreated animals (Table 2).

REFERENCES

Andrews, P. L. R. and C. J. Davis (995). In: *Serotonin and the scientific basis of anti-emetic therapy* (Reynolds D. J. M., Andrews P. L. R. and Davies C. J., Eds.) pp. 25–49. Oxford Clinical Communications, Oxford.

Correa-Sales, C., C. Nacif-Coelho, K. Reid and M. Maze. Inhibition of adenylate cyclase in the locus cocruleus mediates the hypnotic response to an alpha$_2$ agonist in the rat. J. Pharmacol. Exp. Therap. 263: 1046–1049, 1992.

Clineschmidt, B. V., D. J. Pettibone, V. J. Lotti, H. B. Hucker, B. M. Sweeney, D. R. Reiss, E. V. Lis, J. R. Huff and J. Vacca. A peripherally acting alpha-$_2$ adrenoceptor antagonist: L-659,066. J. Pharmacol. Exp. Therap. 245: 32–40, 1988.

Fish, R. E. Pharmacology of Injectable anesthetics. In: Anesthesia and analgesia in laboratory animals. D. F. Kohn, S. K. Wixson, W. J. White & G. J. Benson (eds.) American College of Laboratory Animal Medicine Series, Academic Press, New York, 1997. pp.1–28.

Flecknell P. Laboratory Animal anesthesia. Academic Press Ltd, London, 1996. pp.274.

TABLE 2

Effect of the alpha$_2$ adrenoceptor agonist, clonidine, on behavioral effects observed following the administration of RS14203 in ferrets.

| Pre-treatment | Dose μg/kg | Emetic agent | Salivation | Hyperventilation | Gags | Clawing |
|---|---|---|---|---|---|---|
|  |  |  | (n° responders/n° tested) | | | |
| vehicle | — | RS14203 | 6/6 | 6/6 | 6/6 | 6/6 |
| clonidine | 62.5 | RS14203 | 2/3 | 2/3 | 1/3 | 2/3 |
|  | 125 | RS14203 | 1/3 | 2/3 | 1/3 | 1/3 |
|  | 250 | RS14203 | 0/6 | 1/6 | 5/6 | 5/6 |

In the clonidine 250 μg/kg pretreated group, none of the animals experienced salivation and one out of six showed hyperventilation following RS14203 administration. Gags and clawing at the mouth, however, were not influenced.

Harbinson, P. L., D. MacLeod, R. Hawksworth, S. O'Toole, P. J. Sullivan, P. Heath, S. Kilfeather, C. P. Page, J. Costello, S. T. Holgate & T. H. Lee. The effect of a novel orally active selective PDE 4 isoenzydineme inhibitor (CDP840) on allergen-induced responses in asthmatic subjects. *Eur. Respir. J.* 10: 1008–1014, 1997.

Heaslip R. J. and Evans D. Y. (1995) Emetic, central nervous system and pulmonary activities of rolipram in the dog. *Eur. J Pharmacol.* 286: 281–290.

Hisaka, Y., S. Ogasawara and K. Takase. Alpha adrenoceptor subtypes involved in the emetic action in dogs. J. Pharmacol. Exp. Therap. 261:746–754, 1992a.

Hikasa, Y., T. Akiba, Y. Iino, M. Matsukura, K. Takase and S. Ogasawara. Central a-adrenoceptor subtypes involved in the emetic pathway in cats. Eur. J. Pharmacol. 229: 241–251, 1992b.

Hikasa, Y., K. Takase and S. Ogasawara. Evidence of the involvement of $a_2$-adrenoceptors in the emetic action of xylazine in cats. Am. J. Vet. Res. 50: 1348–1351, 1989.

Horowski R. and Sastre-y-hernandez M. (1985) Clinical effects of neurotropic selective cAMP phosphodiesterase inhibitor rolipram in depressed patients: global evaluation of the preliminary reports. *Current Therapeutic Res.* 38: 23–29.

Humpel M,. Kühne G., Lehmann M. and Poggel A. (1986) Pharmacokinetically governed design of animal toxicity studies of a new antidepressant drug. *Arch. Toxicol.* 9: 251.

Japundzic-Zigon, N., R. Samardzic and D. B. Beleslin. Clonidine-induced emesis: a multitransmitter pathway concept. Pharmacol. Res. 35: 287–297, 1997.

Karlsson, J-A. and D. Aldous. Phosphodiesterase 4 inhibitors for the treatment of asthma. Exp. Opin. Ther. Patents. 7:989–1003, 1997.

Khandker, S. K., D. Mukerjee, S. Gurtu, K. K. Pant, K. N. Dhawan and J. N. Sinha. Modification of reserpine-induced emetic response in pigdeons by a2-adrenoceptors. Pharmacol. Res. 29:383–387, 1994.

Langer, S. Z. Presynaptic regulation of the release of catecholamines. Pharmacol. Rev. 32: 337–361, 1981.

Murdoch, R. D., Cowley H., Upward J., Webber P. and Wyld P. (1998) The safety and tolerability of Ariflo™ (SB207, 499), a novel & selective phosphodiesterase 4 inhibitor, in healthy male volunteers. *Am. J. Respir. Crit. Care Med* 157: A409.

Nicholson C. D. and Shadid M. (1994) Inhibitors of cyclic nucleotide phosphodiesterase isoenzydinemcs—their potential utility in the therapy of asthma. *Pulmon Pharmacol* 7: 1–17.

Nieman R. B., Fisher B. D., Amit O. and Dockhorn R. J. (1998) SB207,499 (Ariflo™), a second generation, selective oral phosphodiesterase type 4 inhibitor, attenuates exercise induced bronchoconstriction in patients with asthma. *Am. J. Respir. Crit. Care Med.* 157: A413.

Pettibone, D. J., B. V. Clineschmidt, V. J. Lotti, J. J. Baldwin, J. R. Huff, W. C. Randall, J. Vacca and S. D. Young. Nauny-Schmicdeberg's Arch. Pharmacol. 336: 169–175, 1987.

Savoic, C., A. Robichaud, C.-C. Chan and I. W. Rodger. Selective potentiating effect of RS14203 on a serotoninergic pathway in anaesthetised rats. Submitted.

Silvestre, J., A. Graul, J. Castaner. SB-207499. Drugs of the future. 23:607–615, 1998.

Sylvina, T. J., N. G. Berman and J. G. Fox. Effects of yohimbine on bradycardia and duration of recumbency in ketamine/xylazine anesthetized fendineets. Lab. Animal Sci. 40: 178–182, 1990.

Zeller E., Stief H. J., Pflug B. and Sastre-y-hernandez M. (1984) Results of a phase II study of antidepressant effect of rolipram. *Pharmacopsychiatria* 17: 188–190.

All references cited are hereby incorporated by reference in their entirety.

What is claimed is:

1. An assay for emitic activity of a PDE 4 (type 4 phosphodiesterase) inhibiting compound, comprising:
    (A) administering to a test mammal an anesthtic compound in an amount sufficient to cause an anesthetic effect;
    (B) administering to a test mammal a test compound that has PDE 4 inhibitory activity;
    (C) observing the test mammal for changes in the anesthetic effect, and
    (D) correlating any change in the anesthetic effect observed in the anesthetized test mammal to a standard.

2. An assay in accordance with claim 1 wherein the anesthetic compound administered to the test mammal in an amount sufficient to cause an anesthetic effect is an alpha-2 adrenoceptor agonist compound selected from the group consisting of xylazine, medetomidine, dexmedetomidine, detomidine and clonidine.

3. An assay in accordance with claim 1 wherein the anesthetic is selected from the group consisting of: ketamine, phenycyclidine and tiletamine.

4. An assay in accordance with claim 1 wherein observing the test mammal for changes in the anesthetic effect is comprised of observing the anesthetized mammal for restoration of the righting reflex.

5. An assay in accordance with claim 4 wherein the restoration of the righting reflex is correlated with the propensity of the test PDE 4 inhibiting compound to cause emesis.

6. An assay in accordance with claim 1 wherein the test mammal is selected from the group consisting of: rats, mice and ferrets.

7. A method for selecting a test compound for its ability to cross the blood-brain barrier comprising:
    (A) administering to a test mammal an anesthetic compound in an amount sufficient to cause an anesthetic effect;
    (B) administering to the test mammal a test compound;
    (C) observing the test mammal for changes in the anesthetic effect, and
    (D) correlating any change in the anesthetic effect observed in the anesthetized test mammal to a standard, wherein said change in said anesthetic effect in the test mammal when compared to a standard is an indication of the test compound's ability to cross the blood-brain barrier.

8. An assay in accordance with claim 7 wherein the anesthetic compound administered to the test mammal in an amount sufficient to cause an anesthetic effect is an alpha-2 adrenoceptor agonist compound selected from the group consisting of xylazine, medetomidine, dexmedetomidine, detomidine and clonidine.

9. An assay in accordance with claim 7, wherein the anesthetic is selected from the group consisting of: ketamine, phenycyclidine and tiletamine.

10. An assay in accordance with claim 7, wherein observing the test mammal for changes in the anesthetic effect is comprised of observing the anesthetized mammal for restoration of the righting reflex.

11. An assay in accordance with claim 10, wherein the restoration of the righting reflex is correlated with the ability of the test compound to cross the blood-brain barrier.

12. An assay in accordance with claim 7 wherein the test mammal is selected from the group consisting of: rats, mice and ferrets.

* * * * *